United States Patent [19]
Fagerhol et al.

[11] Patent Number: 5,455,160
[45] Date of Patent: Oct. 3, 1995

[54] DIAGNOSTIC TEST AND KIT FOR DISEASE OR DISORDERS IN THE DIGESTIVE SYSTEM

[76] Inventors: Magne K. Fagerhol, Konsul Schjelderupsvei 7, 0286 Oslo; Inge Dale, Kirkehaugsvn. 1, 0283 Oslo; Arne G. Røseth, Kollemn. 11 A, 1315 Nesoya, all of Norway

[21] Appl. No.: 67,802

[22] Filed: May 27, 1993

[51] Int. Cl.$^6$ ............... G01N 33/53; G01N 33/574
[52] U.S. Cl. ............... 435/7.23; 435/7.92; 435/7.93; 435/961; 436/64; 436/811; 436/813
[58] Field of Search ............... 435/7.23, 7.92, 435/7.93, 961, 975; 436/64, 811, 813, 815

OTHER PUBLICATIONS

Roth, J. et al, *Biochem. Biophys. Res. Comm.*, vol. 191, No. 2, pp. 565–570, Mar. 1993.
Brandtzaeg, P., et al., *J. Clin. Pathol.*, vol. 41, No. 9, pp. 963–970, Sep. 1988 (Abstract).
Roth, J., et al., *Immunobiology*, vol. 186, No. 3–4, pp. 304–314, Nov. 1992, (abstract only).
Røseth, A. G., et al., "Assessment of the Neutrophil Dominating Protein Calprotectin in Feces," *Scand. J. Gastroenterol.*, vol. 27, No. 9, pp. 793–798, Sep. 1992.
Røseth, A. G., et al., "Fecal Calprotectin: A New Marker of Disease Activity in IBD?" *Scand. J. Gastroenterol.*, vol. 25, Supp. 176, p. 91, 1990.

*Primary Examiner*—Toni R. Scheiner
*Attorney, Agent, or Firm*—Cushman Darby & Cushman

[57] ABSTRACT

This study describes method for extraction and quantification of calprotectin (L1 protein) in feces by enzyme immunoassay. This protein is a prominent antimicrobial component of neutrophils, monocytes, macrophages and squamous epithelia. Calprotectin was stable in feces during storage for seven days at room temperature. Fecal calprotectin quantitated in a five gram sample taken from a 24 hours feces collection gave a reliable estimate of calprotectin found in the pooled collection. The assay had a within assay precision (=CV) of 1,9% and a between assay precision of 14,8%. The following mean fecal calprotectin levels were found: Healthy subjects (n=33) 3095 μg/l, hospital controls (n=40): 14697 μg/l, patients with inflammatory bowel disease (Crohn's disease and ulcerative colitis), (n=28) 40850 μg/l. The differences between the means are highly significant. All patients with IBD and ten out of eleven patients with gastrointestinal carcinomas had calprotectin level above the suggested reference limit of 9000 μg/l. Determination of fecal calprotectin is an important routine parameter for monitoring IBD and gastrointestinal cancer.

7 Claims, 7 Drawing Sheets

1  2  3  4

1  5  6  7

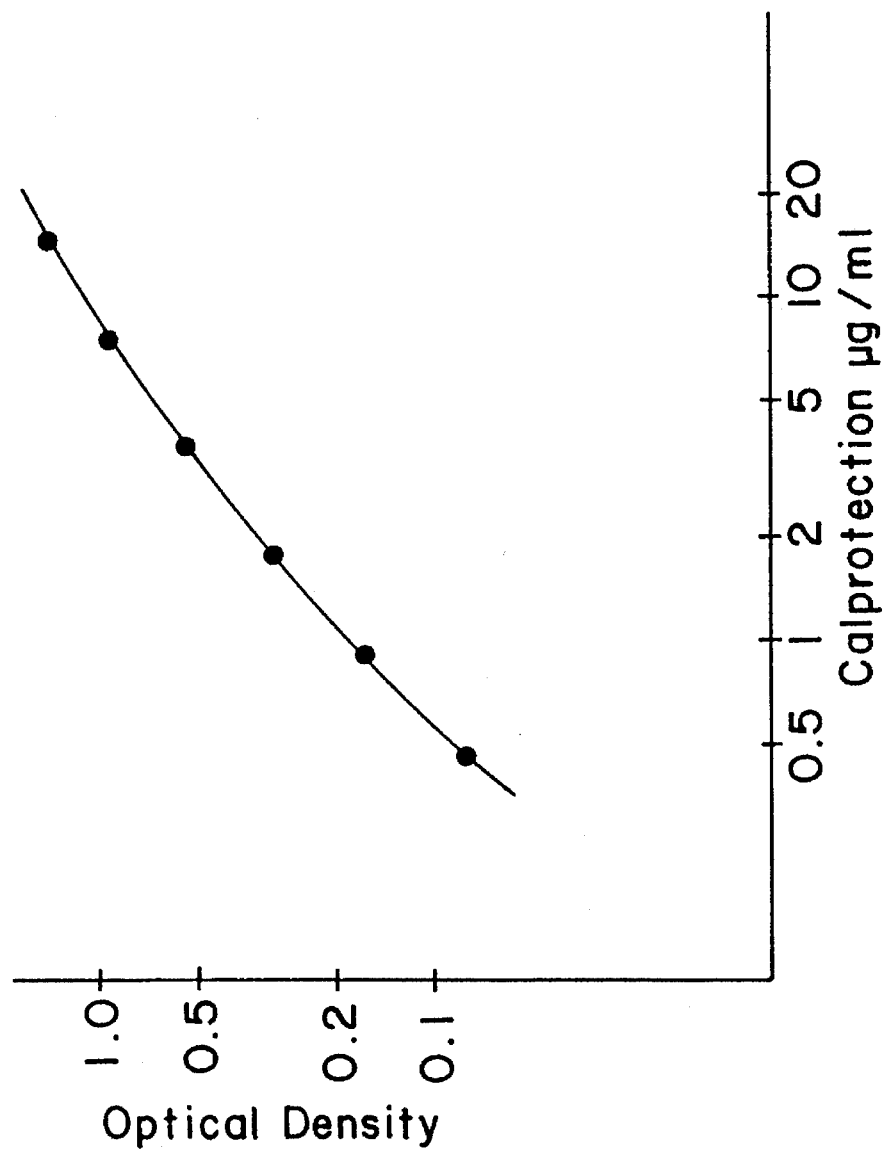

DIAGNOSTIC TEST AND KIT FOR DISEASE OR DISORDERS IN THE DIGESTIVE SYSTEM

FIELD OF THE INVENTION

The present invention relates to a method of diagnosing cancer and other diseases in the gastrointestinal system of mammals, specifically humans, as indicated by increased quantities of calprotectin in fecal samples or samples from the gastrointestinal tract of the mammals. More particularly, the present invention relates to a method of screening for the presence of IBD or gastrointestinal cancer and immunological methods of measuring calprotectin.

BACKGROUND OF THE INVENTION

A method for objective assessment of disease activity in Inflammatory Bowel Disease (IBD) might facilitate the management of patients as well as the evaluation of therapeutic trials. Over the years, several different clinical and laboratory indices including radioactive scanning techniques have been used to determine disease activity in IBD (1–13). The labelling of leucocytes with the radioactive isotopes $^{111}$Indium and $^{99}$Technetium has given promising results, and fectal excretion of these isotopes has been regarded as the "gold standard" of disease activity in IBD (14–15). Despite their high sensitivity and specificity, these techniques have limitations; they are cumbersome, costly, and expose the patient, especially the liver and spleen, to radiation (11, 16, 17, 18, 19). For these reasons the use of isotope techniques are not recommended in children, adolescence and fertile women (13, 21).

BRIEF DESCRIPTION OF THE DRAWINGS

FIG. 8 shows standard curve with the regression parameters and statistics for the rat calprotectin enzyme immunoassay. LOG (OD) versus LOG (Concentration).

Regression Equation

Regression Parameters, Statistics and Results

Log $(OD)$ = $-4.921270000E+00$ +

$1.827302000E+00$#Log $(C)$ $-1.473436000E-01$# $(Log(C))$ 2

Figure 1:
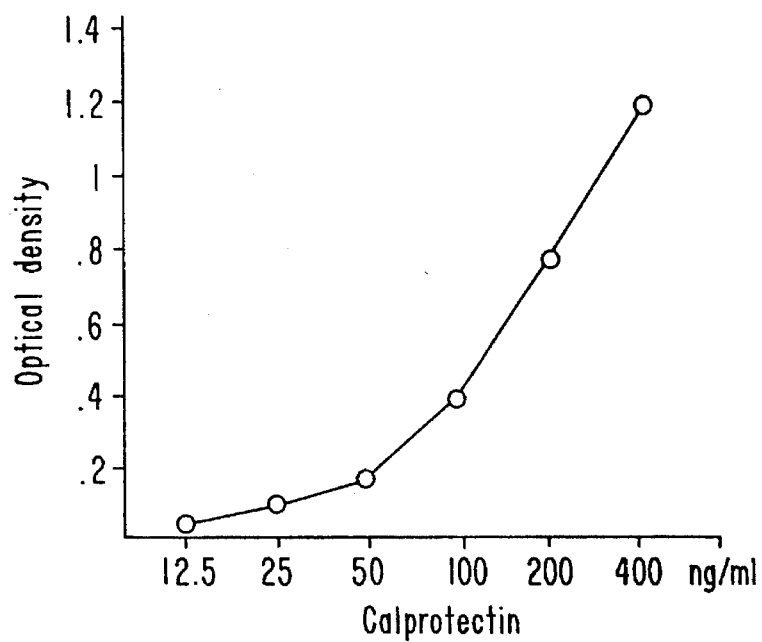
FIG. 1 shows a typical standard curve for the calprotectin EIA; calprotectin levels are on a log scale.

Coefficient of determination=1,000
Coefficient of correlation=1.000
Standard error of estimate=0.006
Comparison of the Standard Data with the Regression Prediction.

|   |            | Measured | Predicted |
|---|------------|----------|-----------|
| S | 115000.000 | 1.372    | 1.381     |
| S | 27500.000  | 0.900    | 0.885     |
| S | 33750.000  | 0.528    | 0.534     |
| S | 41875.000  | 0.306    | 0.303     |
| S | 5938.000   | 0.160    | 0.162     |
| S | 6469.000   | 0.081    | 0.081     |

DETAILED DESCRIPTION OF THE INVENTION

Calprotectin is a major protein in neutrophilic granulocytes and macrophages (22), and accounts for as much as 60% of the total protein in the cytosol fraction in these cells (23).

It is also present in squamous epithelial cells of mucous membranes and most squamous epithelial cancers, but not in normal skin. It will, however, appear also in the latter in most types of skin diseases. Also it may appear in some adenomateous and sarcomatous cancers.

This protein, earlier referred to as L1 protein, consists of two heavy and one light chain, has a molecular mass of 36 kiloDaltons (24) and can bind six calcium atoms. (23) In association with $Ca^{++}$, calprotectin is resistant to proteolyric enzymes as well as heat (23).

Lately, it has been demonstrated that calprotectin has antimicrobial properties, both bactericidal as well as fungicidal, and with minimal inhibitory concentration comparable to those of several antibiotics (25). A significant difference in plasma calprotectin levels has been demonstrated in men and women (24). Plasma calprotectin increases five to forty fold in conditions like septicemia, malignant lung disease (23), rheumatoid arthritis (26) and ISn (27).

While looking for a marker of fecal leukocytosis we discovered high levels of calprotectin in stools from patients with IBD. We have followed up that finding, and developed methods for extraction and assessment of fetal calprotectin. Whether fecal calprotectin level reflects leucocyte activation and turnover in the gut wall has not yet been determined, but if so, it might be a useful parameter in the diagnosis and follow-up of patient with IBD.

Materials and Methods

Groups Studied

Stool stamples were collected during 24 hours from 33 healthy volunteers, 28 patients with IBD (20 with Crohn's disease, eight with ulcerative colitis) and 40 patients with other diseases. The patients with IBD were unselected with regard to age, localization or disease activity. Patients with acute infections, intoxications or using either non-steroidal anti-inflammatory, cytotoxic or thyrostatic drugs were excluded. The non-IBD group comprised the following diagnoses and number of patients: rheumatoid arthritis (10), bronchial carcinoma (4); chronic obstructive lung disease (1), irritable bowel syndrome (9), carcinoma of the colon (8), gastric cancer (2), oesophageal cancer (1), liver cirrhosis (2), pancreatitis (1), lymphoma (1) and tracheal stenosis (1). The age and sex distribution of the subjects is shown in Table 1.

TABLE 1

Demographic data on the groups studied.

| GROUPS: | No. | M/F | x age in yrs. | Range in yrs. |
|---|---|---|---|---|
| Healthy subjects | 33 | 15/18 | 40 | 17–60 |
| Control patients | 40 | 19/21 | 59 | 21–88 |
| Crohn's disease | 20 | 10/10 | 31 | 14–58 |
| Ulcerative colitis | 8 | 5/3 | 33 | 46–23 |

Materials

The following feces extraction buffer was used: Tris buffered istonic saline, with 10 mM $CaCl_2$ and 0,25 mM thimerosal as antimicrobial agent, pH 8,4. Microtiter plates were supplied by Nunc, Denmark. Rinsing buffer for microtiter plates: 50 mM Tris, 150 mM NaCl, 0,5 mM $MgCl_2$, 2,5 mM KCl, 0,25 mM thimerosal, 0,05% Tween-20, pH 8,0. Assay buffer: As rinsing buffer but with 10 g/l bovin serum albumin, pH 8,0. Substrate buffer: 10% dletanolamine with 0,5 mM $MgCl_2$, 0,25 mM thimerosal, pH adjusted to 9,6 with HCl.

Calprotectin was purified by a novel anion exchange chromatography method. Briefly, cytosol fractions from human neutrophil granulocytes, were run on a DEAE-Sepharose Fast Flow (Pharmacia, Uppsala, Sweden) column taking advantage of the great shift in pI of calprotectin when the protein is allowed to bind calcium (24,25).

IgG fractions from rabbit anti-calprotectin (24) was prepared by affinity chromatography on Protein A Sepharose (Pharmacia, Sweden). Affinity purified anti-calprotectin was subsequently prepared by immobilized calprotectin using an ImmunoPure® Ag/Ab Immobilisation Column (Pierce, USA).

Alkaline phosphatase conjugated calprotectin was prepared with ImmunoPure® Activated Phosphatase (Pierce USA). 15 mg substrate tablets containing p-nitrophenyl phosphate was supplied by Sigma (USA).

Collection of Stools and Preparation of Stool Extracts

Stools were collected in plastic containers and immediately frozen below −20° C. In order to prepare extracts, the stools were thawed and 5 (±0,03) grams aliquots were collected, suspended with 10 ml of fecal extraction buffer and homogenized on ice for one minute at 20000 rpm, using an Ultra Turrax mechanical homogenizer from IKA Werke, Germany. The temperature was maintained between 20° C. and 23° C. during this procedure. Routinely, homogenization for one minute was used since the yield did not increase beyond that period. Variation In results due to heating during this period is unlikely since the temperature rose only from 21° C. to 23° C. after homogenization for five minutes.

The homogenates were centrifuged at 45000 g for 20 minutes at +4° C. and the top halves of the supernatants were pipetted off, frozen and kept below −20° C. until further use.

Quantitation of Calprotectin by Enzyme Immuno Assay (EIA)

Microtiter plates were coated by adding 200 μl of an IgG fraction of a rabbit anticalprotectin diluted 1:1000 in PBS, to each well. The plates were covered with mylar foil and kept at +4° C. until use. Storage between 1 hr and several months has given consistent results. Calprotectin standards, 12,5–400 ng/ml, were prepared by diluting purified calprotectin in assay buffer. Before use, the microtiter plates were washed four times in rinsing buffer. The frozen fecal extracts were thawed, and diluted 1:50 and 1:250 in assay buffer. Mixtures of 50 μl standards or samples together with 50 μl ALP-conjugated anti-calprotectin (diluted 1:400) were shaken at room temperature for 45–60 minutes. Subsequently, the wells were washed four times and 100 μl substrate solution was added. The optical density (OD) at 405 nm of the highest standard was monitored and the reaction was stopped by adding 50 μl of a 1 M NaOH solution to each well when it's OD read between 1.2–1.4. Registration of data and calculations were performed using an Immunosoft (Dynatec USA) program on a personal computer.

A typical standard curve is shown in FIG. 1. Standard errors of estimates were typically between 2 and 5 per cent.

Distribution of Calprotectin in Stools

To determine if calprotectin is evenly distributed in feces, the calprotectin concentrations in three random aliquots of feces were compared with the concentration in thoroughly blended stools. Three random aliquots of 5,0 grams were taken from each portion of stools (=spot samples) and treated as described. The rest of the stools were diluted in fetal extraxtion buffer and thoroughly blended for 1 minute on a commercial blender. An aliquot was sampled from each suspension (= blended samples) and extracts were prepared as described.

Stability of Calprotectin in Feces

Calprotectin levels were determined in extracts prepared from stool samples stored at +4° C. or +20° C. for 24 hours, 48 hours or one week.

Within Assay Variation of the EIA

Extracts with low, medium or high concentration of calprotectin were tested ten times on the same microtiter plate and the coefficient of variation was calculated.

Between Assay Variation

Extracts from 15 patients were tested ten times. Each time fecal dilutions and standard dilutions were freshly made and tested on different microtiter plates.

Statistical Analysis

The Pearson correlation coefficient was calculated for the association between spot samples and the blended samples. The Wilcoxon signed rank test was chosen for evaluation of stability of calprotectin during storage. Student t-test was used to evaluate the difference in means between the various groups studied. For all comparisons p-values less than 0,05 was considered significant.

Results

Distribution of Calprotectin in Stools

The values for the three randomly collected samples were similiar to the values found in blended feces. The correlations between the spot sample one, two and three and the corresponding blended sample were calculated separately. The Pearson's correlation coefficient varied between 0,90 and 0,95 (Table 2).

TABLE 2

The correlation between calprotectin concentration in spot samples and the corresponding fecal homogenate.

|  | MEDIAN DIFFERENCE (%) | CORRELATION COEFF. (r) |
|---|---|---|
| Sample 1 | 20,0 | 0,95 |
| Sample 2 | 21,4 | 0,90 |
| Sample 3 | 21,9 | 0,95 |

Figure 2:
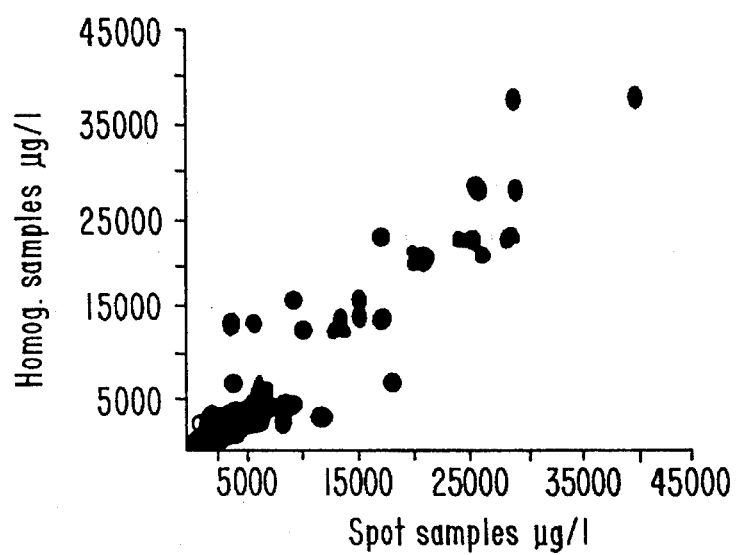
FIG. 2 shows the correlation between calprotectin in three spot samples and their corresponding fecal homogenate (n=48).

Median percentual difference was approximately 21%. A scatter diagram showing the correlation between calprotectin in randomly collected samples and in blended stools is presented in FIG. 2.

Assay Reproducibility

Our data show a between assay variation of 14,8%, and a within assay variation of 1,9%.

Stability of Calprotectin in Stools

Figure 3:
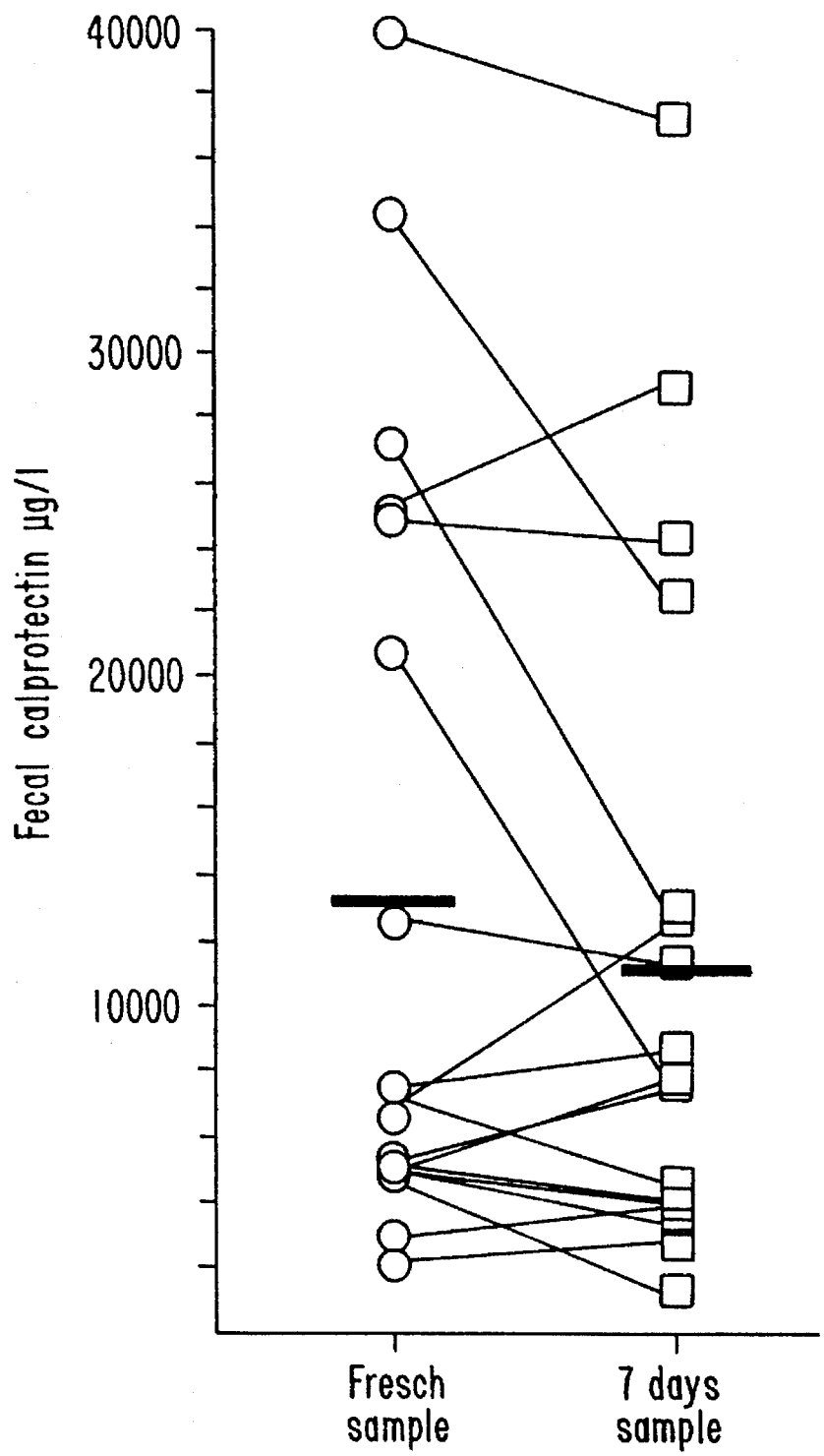
FIG. 3 shows fecal calprotectin concentrations before and after seven days of storage at 20° C.; horizontal lines indicate the two group means.

When stools were stored at +4° C. for 48 hours or at +20° C. for 24 hours no significant alteration in calprotectin levels was observed. After 48 hours at +20° C. a significant (P<0,01) decrease of 17,5% was found. However, after seven days at +20° C. this difference was no longer detectable (FIG. 3).

Fecal Calprotectin Values in the Different Groups Studied

The mean value for fecal calprotectin in the healthy subject group was 3200 µg/l with a S.D. of 2900. This suggests an upper reference limit (Mean ± 2 S.D.) of 9000 µg/l. The mean value for patients with diseases other than IBD was 14637 µg/l, which is significantly higher (P<0,001) than in the healthy subject group. The mean values in patients with Crohn's disease and ulcerative colitis were 45250 µg/l and 36428 µg/l respectively; both are significantly higher (P<0,001) than the two other group means just mentioned (Table 3).

TABLE 3

Concentration of fecal calprotectin (µg/l) in the different groups studied.
P-values refers to comparisons with healthy subjects

| GROUPS: | N | MEAN | RANGE | S.D. | p |
|---|---|---|---|---|---|
| Healthy subjects | 33 | 3200 | 500–8000 | 2906 | — |
| Control patients | 40 | 14637 | 700–50000 | 13785 | <0,001 |
| Crohn's disease | 20 | 45000 | 10000–80000 | 20837 | <0,001 |
| Ulcerative colitis | 8 | 36428 | 18000–80000 | 21030 | <0,001 |

Figure 4:
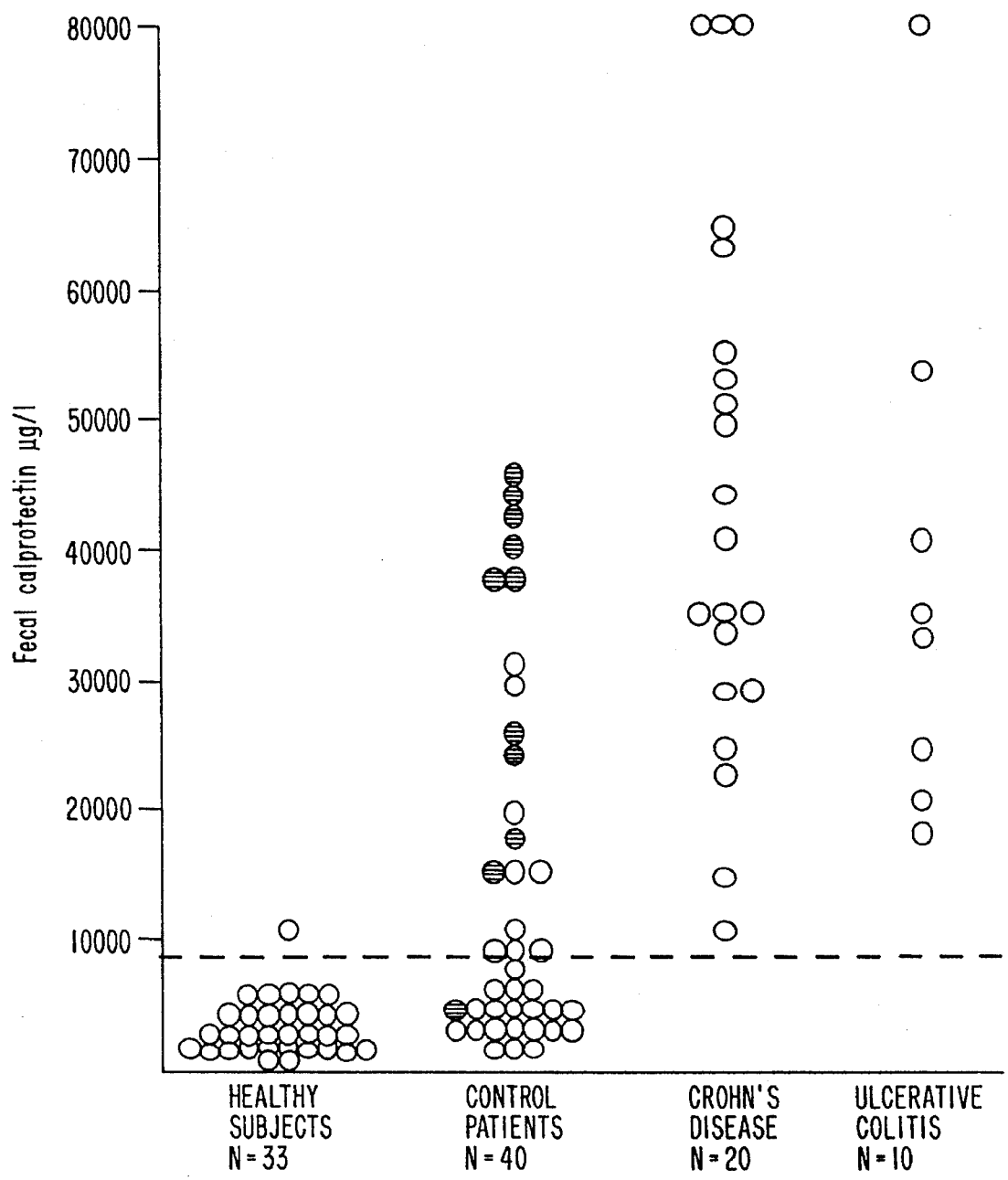
FIG. 4 shows calprotectin concentrations in fecal samples from healthy subjects, control patients and patients with Crohn's disease and Ulcerative Colitis. Patients with gastrointestinal carcinoma are marked with ; dotted line indicates upper reference limit.

The individual values of fecal calprotectin in the four groups studied are shown in FIG. 4.

The non-IBD group included eleven patients with gastrointestinal carcinoma. As shown in FIG. 4, ten of these cancer patients had fecal calprotectin levels above the upper reference limit: mean value was 30 600 µg/l, the range 6000/46000 µg/l. This was significantly higher (P<0,001) than the mean of the healthy subjects, as well as the mean of the non-IBD patients (P<0,001), but lower (P<0,05) than the group mean of patients with Crohn's disease.

Discussion

This study was initiated because we felt that previous methods to monitor disease activity in IBD patients were unsatisfactory. A critical review of the literature also revealed a concensus that the clinical indices are insufficient in determining the disease activity at a given time in a patient (4,10,11,15,28,29,30).

Figure 5:
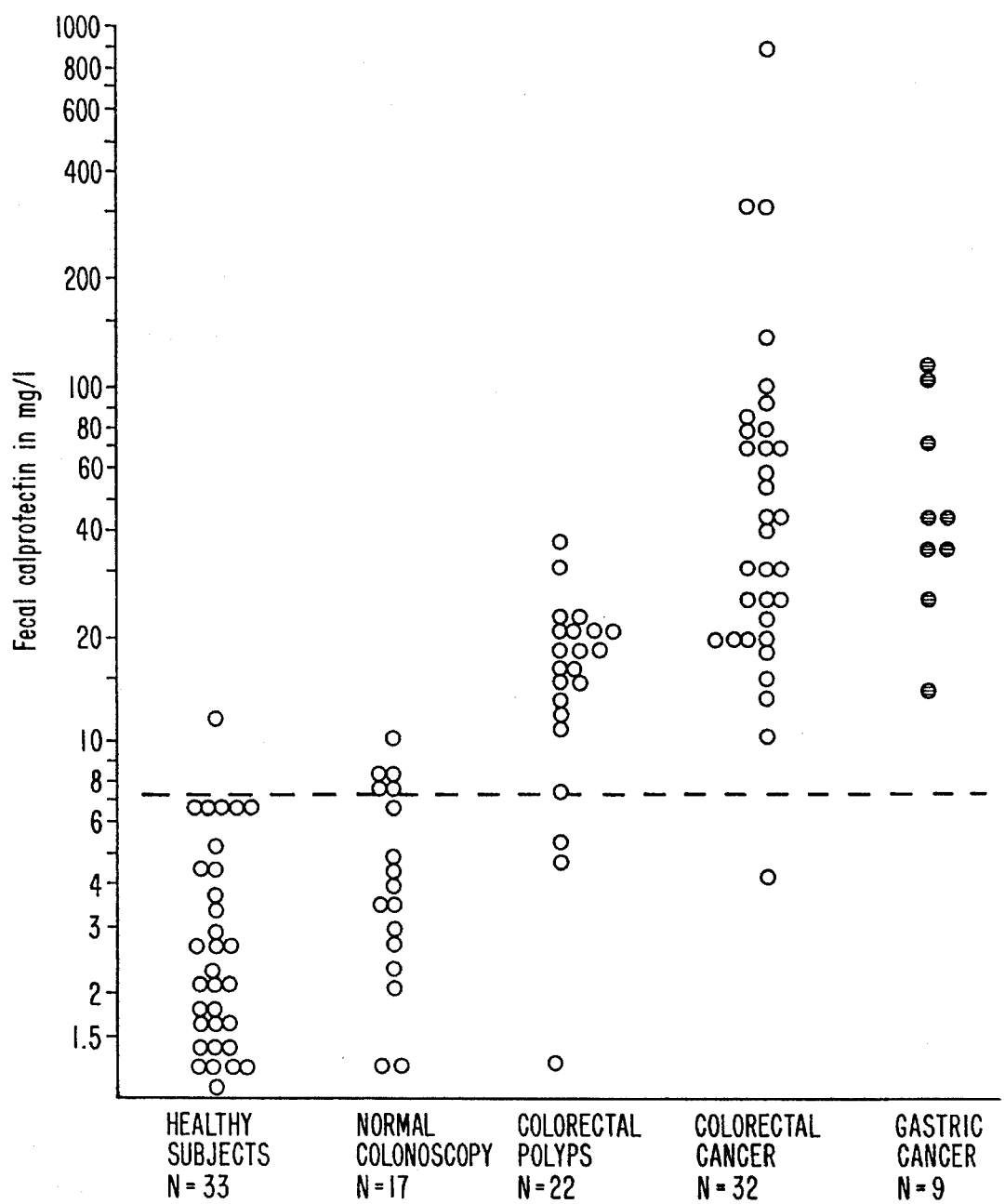
FIG. 5 shows results of a study of cancers of the stomach and the large bowel (gastric and colorectal cancers) as well as polyps known to be early stages or precursors of colorectal cancers.

In a further study and as shown in FIG. 5, we have tested cancers of the stomach and the large bowel (gastric and colorcoral cancers) as well as polyps known to be early stages or precursors of colorcoral cancers. Nine out of nine with gastric cancer had a positive test and 31 out of 32 with colorcoral cancer had a positive test. Eighteen out of twentytwo with polyps had a positive test. All the patients tested were nonselected, consecutive patients referred for colonoscopy or newly discovered cancer patients admitted for primary surgical treatment. This is, to our knowledge, the first fecal test which can detect both polyps and gastric cancers. Also, it has about twice the sensitivity of former tests for colorectal cancer.

To see if other scientists could confirm our findings, we recently sent our reagents and method descriptions to one of the world's leading departments for gastrointestinal diseases (at The Royal Melbourne Hospital, Australia). The results they reported back were remarkably similar to ours: the mean faecal calprotectin level in twenty patients with colorcoral cancers was 47 mg/L, while the mean in our group is 45 mg/L.

Segal (8) and Saverymutto (9) were the first to report that autologous granulocytes labelled with $^{111}$Indium made it possible to both visualize and quantitate the granulocyte turnover in the gut of patients with IBD. These findings have been confirmed by several other investigators ( 10, 12, 14, 15, 15).

We have chosen to study fecal levels of a dominating leukocyte protein which is known to be released in large amounts to lymph, Joint fluid and plasma during activation of such cells. (23, 26) The relatively high calprotectin levels in stools are compatible with data suggesting that in normals the majority of neutrophils migrate through the mucosal membrane of the gut wall and thereby terminate their circulating life (31). In view of the antimicrobial properties of this protein, this may suggest that calprotectin contributes to the regulation of the microbial flora in the intestines. In IBD one would expect an increased turnover of leukocytes in the gut wall as well as increased migration of such cells into the gut lumen (8, 15).

The present study comprises efforts to develop a reliable method for estimation of fecal calprotectin. We have chosen a fetal extraction buffer with pH 8, since calprotectin is more stable in alkaline solution (23). Calcium was added since $Ca^{++}$ will expose more antigenic epitopes, and calprotectin is resistant to proteolytic enzymes in the presence of $Ca^{++}$ (23). Thimerosal was added to prevent bacterial growth which could affect calprotectin. One might have expected that calprotectin as other proteins, would be readily degraded by digestive and/or microbial enzymes found in feces. Surprisingly, calprotectin turned out to be quite stable under the conditions chosen. Calprotectin levels in stools did not change significantly during storage at +4° C. for 48 hr, but during storage at room temperature a significant decrease was observed after 48 hours. This observation is puzzling because storage under the same condition for one week caused no significant difference. The explanation for these observations is obscure, but might reflect different processes taking place either sequentially or simultaneously in feces.

Calprotectin might form complexes with other substances so that antigenic sites are blocked, hence decreased estimates will be found. Conversely, increased values might result from splitting up of such complexes. At any rate, the variations were so small (less than one per cent of the differences between the mean values of the groups of individuals tested), that we conclude that calprotectin in feces has excellent storage capabilities. This allows a practical and convenient method of stool sampling. Furthermore, our data clearly show that a randomly collected fetal sample will give a representative estimate of the concentration of calprotectin in the whole stool portion. Hence a cumbersome prolonged stool collection can be avoided. Similar experiences have been made in studies concerning fetal $\alpha_1$-antitrypsin (4,7,32).

One person in the healthy group had 12000 µg/l calprotectin in her stools. In a new sample collected six month later a normal level was found. We have reasons to belive this high value was caused by an upper respiratory tract infection, with productive cough. Furthermore, Crohn's disease was detected in a seemingly healthy adult male. His fecal calprotectin level was 30 000 µg/l. During endoscopy the macroscopic findings were normal but biopsies revealed typical crypt abscesses. Also, a case of the gastric cancer type "Linitis plastica" had a positive fetal calprotectin test, normal endoscopy but positive biopsy findings.

The high calprotectin level in stools from patients with gastrointestinal carcinomas is a novel finding. The mechanism behind is unknown, but the high level may reflect synthesis of calprotectin by the tumor cells or release from surrounding leukocytes. Studies are in progress to see if this increase is related to tumor histology and/or grade and whether it may have diagnostic implications.

Data from isotope studies (8, 9, 10, 12, 13, 15, 19) suggest an increased intestinal turnover of leukocytes in IBD. In view of the great amounts of calprotectin in neutrophils and monocytes/macrophages and its rapid release from such cells during storage and activation, it seems likely that the increased fecal calprotectin levels observed in IBD patients reflect an increased intestinal turnover of such cells.

In our group of patients with IBD the disease activity ranged from complete remission to severe illness causing hospitalization. The three patients with the highest levels of fecal calprotection (about 80 000 µg/l) belonged to the latter group, while the lowest value recorded (about 10 000 µg/l) was found in an individual who had been in remission for more than ten years. This may suggest that fecal calprotectin levels vary with the disease activity in IBD.

II

Colorectal carcinoma is thought to develope from polyps, and should therefore be amenable to early detection as well as secondary profylaxis (33,34). Despite strong efforts, the prognosis of this very common malignancy has not changed noticeably over the past three decades (35,36). The fecal occult blood test (FOBT) is commonly used as a screening test for colorectal carcinoma. However, the sensitivity of 50% (4,5), the positive predictive value of 4–14% (35,37) both indicate the need for a simple test with higher accuracy.

Calprotectin (=L1 protein), a 36,5 kDa calcium binding, antimicrobial protein, is mainly found in neutrophils, monocytes and squamous epithelium of mucous membranes (22, 23, 25).

We have recently, according to the invention, developed an enzyme immuno assay (EIA) for quantitation of calprotectin in stools (38). In that study we found that calprotectin was stable in feces during storage for seven days at room temperature, and that total calprotectin could be accurately estimated from small five gram fetal samples. During the first trials of this method, measuring fetal calprotectin in a broad group of hospitalized patients, we found remarkably high levels in patients with colorectal carcinomas (38). This encouraged us to undertake further studies to investigate whether fecal calprotectin might be a useful marker of colorcoral carcinoma, and the following is about these findings, the distribution of calprotectin in malignant tissues and stools from such patients.

Material and Methods

Twenty consecutive hospitalized patients with CRC were studied, thirteen men, mean age 65 years, range 47–85 years and seven women, mean age 73 years range 62–82 years.

TABLE 4

Demographic data of study group.

| No. | M/F | Mean age | Localization | Preop. metast. | Alive |
|---|---|---|---|---|---|
| 6 | 2/4 | 72 | Coecum | 1 | 2 |
| 2 | 2/0 | 56 | Trans.descend. | 1 | 1 |
| 4 | 1/3 | 66 | Sigmoideum | 0 | 4 |
| 8 | 7/1 | 70 | Rectum | 1 | 7 |

Tumour staging and histological examination were performed by standard, conventional methods using haematoxylin-eosinophil staining technique. Ultrasound examination of the liver and a chest X-ray were performed on all patients prior to surgery.

Feces was sampled at admission to hospital. A second sample was obtained from eleven patients three to six months after surgery. Six patients died (five from cancer, one from postoperative complications) and were therefore not available for the follow up testing. Five gram fecal sample were mixed with ten ml of trisbuffered saline containing 10 mM $CaCl_2$ and 0,25 mM thimerosal, pH 8,4. Thereafter it was homogenized (on ice) for one minute at 20 000 rpm with an Ultra Turrax (IKA Werke, Germany). The homogenate was centrifuged at 45 000 g for 20 min at +4° C. The top halves of the supernatant were recovered and kept at –20° C. until use. Calprotectin quantification was performed by the following EIA: Microtiter wells were coated by an IgG fraction of a rabbit anticalprotectin isolated on a protein-A-sepharose (Pharmacia, Sweden) column. Each well was filled with 200 µl IgG fraction diluted 1:1000 with phosphate buffered saline with 0,25 mM thimerosal, pH 7,4. The plates were kept under mylar foil and stored at +4° C. Before use, the wells were washed three times with the following rinsing buffer: 50 mM tris, 150 mM NaCl, 0,5 mM $MgCl_2$, 2,5 mM KCl, 0,25 mM thimerosal, 0,05% (v/v) Tween-20, pH 8,0. Samples and standards (purified calprotectin) were diluted in assay buffer which was rinsing buffer with 10 g/l bovine serum albumin, pH 8,0. Rabbit anticalprotectin was affinity purified using calprotectin immobilized on an Immunopure Ag/Ab immobilization (Pierce, USA) column. Then antibodies were conjugated with alkaline phosphatase (ALP) using an Immuno Pure Activated Phosphatase kit (Pierce, USA). During the EIA, 50 µl standards or samples were mixed with ALP conjugated anticalprotectin antibodies (diluted 1:400) and shaken at room temperature for 45 minutes. The wells were then washed three times, then 100 µ/l substrate (1 mg/ml p-nitrophenyl phosphate in 10% (v/v) diethanolamine, 0,5 mM, 0,5 mM $MgCl_2$, 0,25 mM thimerosal, pH 9,6) was added to each of the wells. The reaction was stopped after 10–20 min. by addition of 50 µl/well of 1M NaOH when the OD of the highest standard reached 1,2–1,4. This procedure has a precicion of 14,8% (C.V.) between and 1,9% within assay (38). Histological examination were performed on routinly formaldehyde fixed and paraffin embedded speciments. Immunochemical staining was performed as described by Brandtzaeg et al (22), except the use of immunoaffinity purified anti-calprotectin conjugated with horseradish peroxidase or ALP (see above), and we did not use alcohol for fixation. Substrates were diaminobenzidine and fast red, respectively.

The spesificity of the immunohistochemical staining was confirmed both by blocking with excess purified calprotectin in solution and by incubation with unconjugated anti-calprotectin. In either case the staining was abolished.

Results

All the 20 patients (FIG. 2) had fecal calprotectin concentration above the upper referante limit (=median and 95% confidence interval) of 6,8 mg/l determined in healthy controls (38). The median of the healthy group was two mg/l (38), while the median of the cancer patients was 50 mg/l, a difference which is statistically highly significant ($p<0,0001$) by Wilcoxon). After surgery the median fetal calprotectin levels had dropped to three mg/l. This difference between pre and post operative values is significant ($p<0,03$).

By immunohistochemistry strong staining for calprotectin was seen in many neutrofile granulocytes in the rumour, and strikingly, in capillaries close to the epithelial surface, seemingly in the process of migration into the lumen of the intestinal.

Discussion

Figure 6:
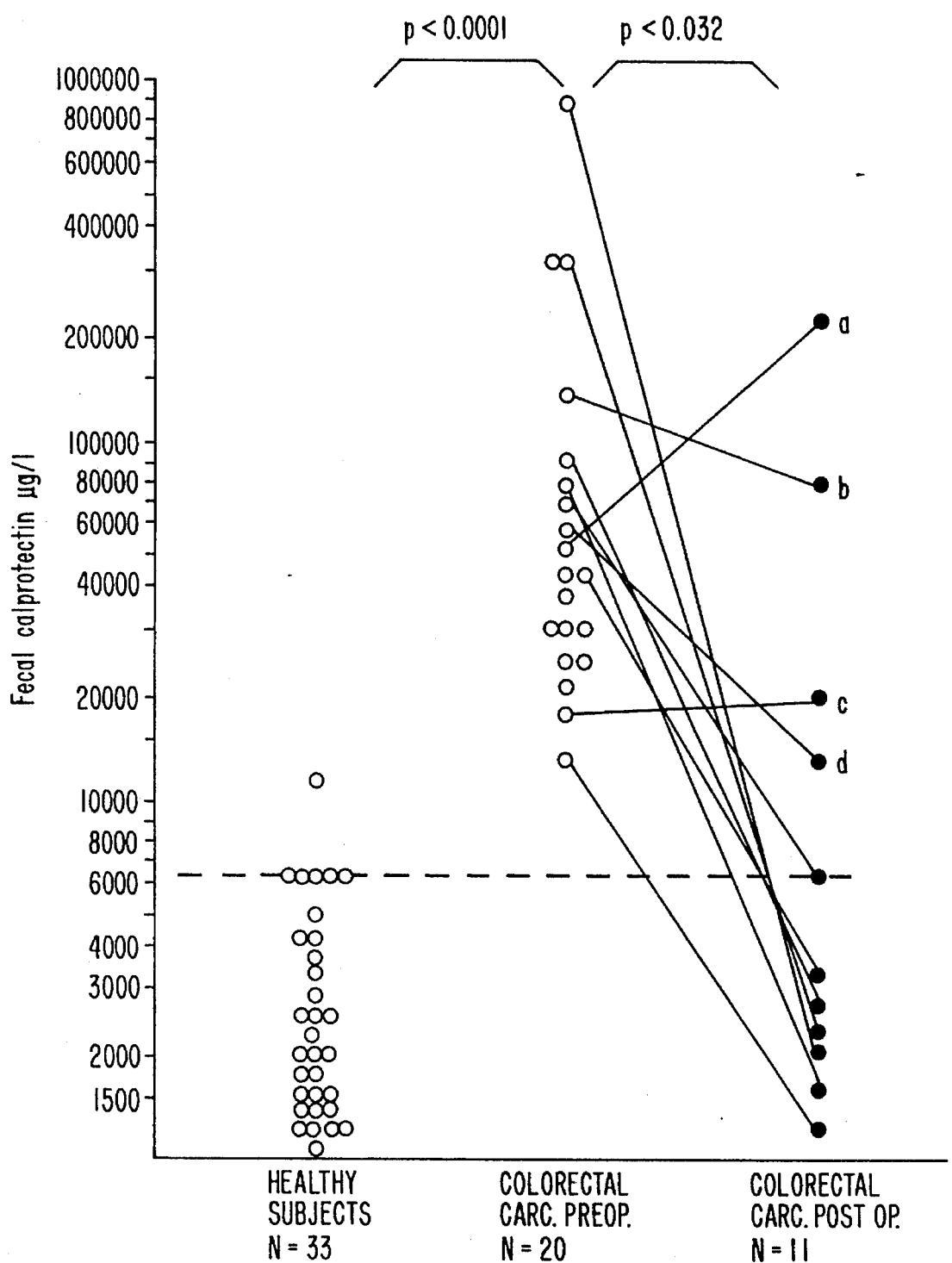
FIG. 6 shows fecal calprotectin in healthy subjects and in patients with CRC, before and after surgery. Values are in µg/l on a log scale, horizontal line indicates upper reference limit for healthy subject.

The finding of increased fecal calprotectin concentrations in all 20 patients with colorectal carcinomas are striking. The calprotectin levels varied from four to three hundered times the normal mean suggesting fetal calprotectin as a promising novel marker for colorectal carcinoma. We reexamined stools from these patients three to six months after surgery to investigate whether calprotectin levels had normalized or not. (FIG. 6). We found that seven out of eleven patients had normal values after surgery.

Patients who had residual tumor after surgery tended to have high levels postoperatively. One patient had a four fold (50—>200 mg/l) increase in fetal calprotectin. This patient was not radically resected and had residual rumour as well as liver metastasis. One patient decreased from 140 mg/l to 76 mg/l, still far over the suggested upper reference limit of 8,2 mg/l. This was an 85 year old patient with a rectal cancer and due to his old age, he was only treated locally with laser surgery and hence, not radically resetted. Two patients, both radically resetted, failed to normalize their fecal calprotectin values. In one patient, the postoperative value of 15 mg/l (down from 60 mg/) might reflect the fact that this patients had rheumatoid arthritis. We have earlier (38) studied such patients, and found that six out of ten had increased values in their fetal calprotectin. The last patient showing little change (17—>20 mg/l) had multiple diverticulies in the colon. An inflammation in one or several such structures might result in an increased flux of granulocytes into the gut lumen and hence increased fecal calprotectin.

Both sampling and handling of feces is simple, due to calprotectin's even distribution and stability in feces. By comparison, fecal haemoglobin is more readily degraded (33,35), and only about half of colorectal carcinomas do actually bleed, and the rest do not bleed or only intermittently (35). While the sensitivity of fecal calprotectin levels for detection of CRC seems very high (100%), our data are yet too preliminary for calculation of a positive predictive value. However, so far a positive predictiv value of 67% seems promising. Very high levels are also found in patients with Crohn's disease, ulcerative coliris (FIG. 4) as well as in patients with diverticulitis, while a group of patients with other diseases had mostly normal fecal calprotectin concentrations (38). The origin of increased fecal calprotectin in CRC has not yet been completely resolved, although the histological findings may suggest that synthesis by tumor cells is one possibility. Another is release from infiltrating leucocytes, although such infiltrations was not seen or very limited during this study. The large variation found with regard to staining intensity is compatible with the well known heterogeneity among tumor cells and fits nicly with findings by Dale et al (39) while studying calprotectin in tumorcells from pulmonary carcinomas. Since we did not examine every part of the tumors, it is quite possible that calprotectin was present also in discrete areas of the three tumors which was classified as negative in this study. Preliminary data indicate that calprotectin is present in colorectal adenomas. Further studies are in progress to see if this correlates with the degree of cell differentiation, and also to see if this cause increase in fecal levels in such patients. We will also test if this can be useful in selecting patients for colonoscopy.

III

Calprotectin is, as mentioned, a calcium binding heterotrimer 36,5 kDa protein found in neutrophil granulocytes, monocytes/macrophages, squamous epithelial cells and some cancer cells. In neutrophils, it constitutes more than 60% of total soluble cytosol proteins.

It is also found in serum, plasma, cerebrospinal fluid, saliva, urine and feces. In such materials, calprotectin levels are increased as a consequence of various types of diseases.

Figure 7A:
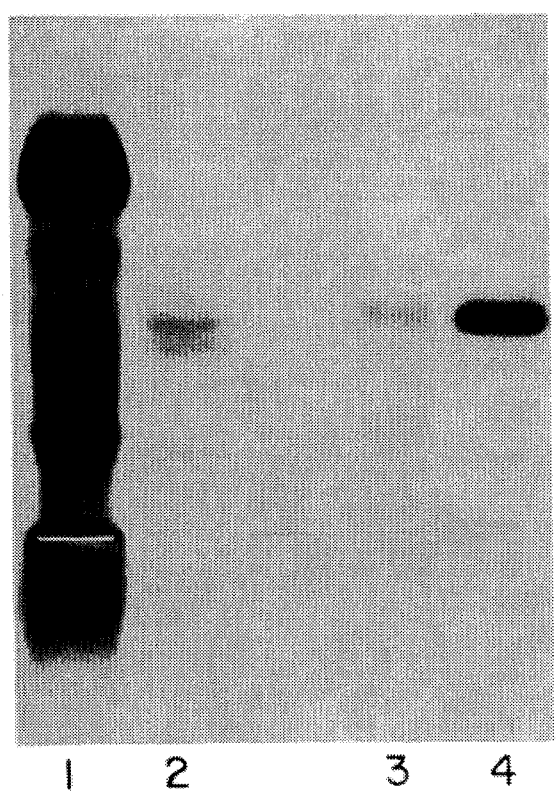
FIG. 7 shows agarose gel electrophoresis, 75 mM barbital buffer, pH 8.6 with 2.5 mM thimerosal. Anode at the top, cathode at the bottom. Samples: 1: Normal serum, 2: purified human calprotectin, 2 mg/ml, 3: purified pig calprotectin, 1 mg/ml, 3: purified pig calprotectin, 0.5 mg/ml, 4: purified pig calprotectin, 20 mg/ml, 5: crude rat leucocyte extract, 6: semipurified rat calprotectin, 7: purified rat calprotectin, 4 mg/ml.
Figure 7B:
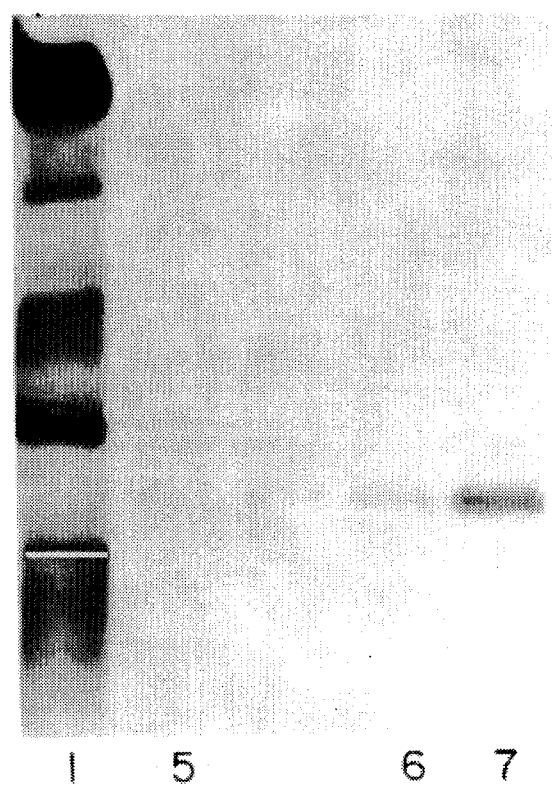

Based upon our previous findings on calprotectin in humans and in sheep (41), we have recently also isolated the corresponding protein in pigs and rats. In FIG. 7 are shown these purified proteins on analytical agarose gel electrophoresis. Each of them has been used for immunization of rabbits; the resulting antibodies have been used for immunohistochemical studies of animal cells and tissues and for establishement of enzyme immunoassays corresponding to the methods described above for the human calprotectin. We have found that in both species calprotectin is present in neutrophil granulocytes, plasma, peritoneal fluid and stools.

In FIG. 8 is shown a typical standard curve for estimation of the rat calprotectin by our enzyme immunoassay. Using this method, we have found that the concentration of calprotectin in stools from rats is very similar to what we have found in humans.

Furthermore, the concentration increases 20–30 times six hours after oral administration of drugs that are known to cause gastrointestinal inflammation. Studies are now in progress to examine calprotectin in stools from rats treated with chemicals that will induce colorectal cancers. Such an experimental cancer model can be used for many different purposes.

The corresponding protein has been found in different animal species like sheep, pigs and rats.

Calprotectin was discovered by our research group which has continued to be in the forefront in this field. A comprehensive summary of our work, with details on the structure, properties and distribution of the protein as well as references to our original scientific papers, is given in the book chapter and doctoral thesis (23, 40).

Initially, we introduced the preliminary name "L1 protein" which will be found in many scientific reports. But when we discovered its prominent biological activity, the name calprotectin was introduced, alluding to its calcium binding and antimicrobial properties.

Calprotectin can be identified and determined quantitatively by many different immunological techniques using polyclonal antibodies raised in rabbits and rats or monoclonals from mice.

Calprotectin will inhibit the growth of, or at higher cocentrations, kill most (if not all) microorganisms, (25). In subsequent unpublished studies, we have found similar cytotoxic effects on all the human cell types we have tested so far, namely lymphocytes, keratinocytes, endothelial cells and the rumour cell line Hep-2. Furthermore, the protein has induced synovitis after intraarticular injection in rats.

Serum contain factors that can inactivate calprotectin, which seems reasonable since patient plasmas often contain 10–40 mg/l calprotectin compared to the minimal toxic concentrations of 4–100 mg/l against human cells and microorganisms. At levels above 5 mg/l, the replication of HIV in cultures of lymphocytes from AIDS patients is completely blocked. At similar concentrations, the proteins synthesis in human cells is blocked.

Since calprotectin is such a prominent protein, representing a novel, regulated cytotoxic principle in man and animals, there is already a rapidly growing interest in methods for its detection and determination by simple, rapid methods both for clinical and research purposes. The following clinical applications are of prime importance:
1) Increased levels in feces as a marker for colorectal cancer.
2) Increased levels in feces as a marker for disease activity in inflammatory bowel disease.
3) Increased levels in plasma as an early marker for pulmonary cancer.
4) Increased plasma levels as a marker for disease activity in rheumatoid arthritis.
5) Increased levels in cerebrespinal fluids for distinction between AIDS encephalitis and opportunistic infections in the central nervous system.
6) Increased levels in urine as a marker for urinary tract infection with renal involvement.
7) Increased release from leucocytes to plasma as a marker for poor biocompatibely of synthetic materials Since the need for a reliable, early marker for gastric and colorectal cancer is so obvious and of prime importance, mainly this application of our invention will be dealt with in the following.

We have developed a method for simple and rapid extraction of calprotectin in feces and its determination by rapid immunological methods. Feces samples are simply mixed with a small volume of buffer. After centrifugation, the supernatant is harvested and used for quantitative assays. Routinely, we run an enzyme immunoassay with a single incubation of 30 minutes at room temperature, but nephelometry or single radial immunodiffusion can also be used. We therefore feel confident that different types of kits, including some for use in primary health care settings, can be designed.

Samples from patients with colorectal cancer, hospital controls and healthy adults have been tested. The results are as follows:

| GROUP | NO. OF INDIVIDUALS | CALPROTECTIN, mG/L | |
|---|---|---|---|
|  |  | Median | Range |
| Healthy adults | 33 | 2 | 0,5–12 |
| Colorectal cancer | 20 | 45 | 12,5–950 |
| Hospital controls | 29 | 3 | 3–32 |

The hospital control group comprised 29 patients with the following diseases: pancreatitis, renal diseases, reumatoid arthritis, chronic obstructive lung disease, cirrhosis of the liver and irritable colon syndrome. On the basis of this group and the 20 patients with colorectal cancer, our fecal calprotectin test show the following diagnostic potential with regard to colorcoral cancer:

| | |
|---|---|
| SENSITIVITY: | 100% |
| SPECIFICITY: | 72% |
| POSITIVE PREDICTIVE VALUE: | 71% |
| NEGATIVE PREDICTIVE VALUE: | 100%. |

More than half of the colorectal cancer patients were tested again about three months after surgery, and all except one had a significant reduction in the fecal calprotectin level. One of the remaining patients had increased levels at follow up and turned out to have residual rumour and possible inflammation.

The high level of calprotectin in feces allow the use of simple and rapid immunological methods. It seems very likely that methods which do not require special instrumentation also can be developed so that the test can be used in the primary health care. Furthermore, we have shown that calprotectin is very stable and evenly distributed in feces, which simplifies sample handling. Reliable estimates are obtained even when feces has been stored at room temperature for one week. Spot samples of five grams or less can be used.

Digestive disorders, dyspepsia and abdominal pain are among the most common problems dealt with in primary health care. Diagnostic consideration and decisions are often based upon rather subjective and insufficient criteria. Nevertheless, the decisions may have dramatic concequences for the patient, in particular if a malignant condition is overlooked. Furthermore, additional diagnostic procedures, like endoscopy, computer assisted tomography or biopsy are relatively expensive, and not readily available at all times in some countries.

In most large clinical series only about 50% of colorectal cancer patients are alive five years after diagnosis and treatment. There is a general consensus that an improved prognosis is dependent upon detection of the cancers at an earlier stage, preferably by non-invasive procedures that can be applied on patients with few or no symptoms.

In such a situation, the need for a simple, rapid, reliable and inexpensive test that can be applied in the primary health care as well as in hospital settings, is obvious.

Detection of occult bleeding by a benzidine or similar test has been used traditionally, but the diagnostic efficiency of such tests are so poor that they are being abandoned.
The calprotectin test according to the invention seem to be an extremely good alternative.

In a group of 20 consecutive patients with colorectal cancers, the test had a sensitivity of 100%. The importance of this finding is highlighted by the fact that this type of cancer is among the top three killing cancers In most developed countries. We therefore feel confident that the calprotectin test will be used in the very near future for cancer screening, for selection of patients for more demanding and expensive diagnostic procedures and for post treatment monitoring. Furthermore, a negative test will be expected in patients with functional abdominal disorders, in contrast to colorectal cancers and inflammatory bowel disease. Up to now, we have tested six patients with gastric cancer, and they all had a positive calprotectin test. It is therefore possible that the test may be useful for this and other types of abdominal cancers as well.

In addition to the above described calprotectin tests mentioned above and which are aimed primarily at diagnosing gastrointestinal cancers or inflammatory bowel disease in humans, the principals of the present invention have further useful applications:

A: Use of calprotectin determinations in animal models for experimental cancer studies.

Calprotectin may be used for the detection of gastrointestinal cancers as well as the response to new drugs or surgical procedures. This will allow sequential studies by a simple, noninvasive method, in contrast to the present procedures where the groups of animals must be killed at different intervals for macroscopic and microscopic studies of abdominal organs.

B: Use of calprotectin determinations in stools from animals to study possible side effects of radiation therapy or potentially new drugs.

It is well known that untoward reactions from the gastrointestinal tract are among the most common and troublesome side effects of radiation therapy for cancers. Symptoms may start shortly after therapy or after a lag period of many years, and may initially be vague so that the correct diagnosis is often delayed. Cytotoxic drugs often cause similar damage and symptoms. But also drugs used for many different types of diseases cause similar side effects. For instance, the commonly used non-steroid anti-inflammatory drugs (NSAIDs) used against rheumatic diseases, other types of joint problems or even simple headaches, cause gastrointestinal irritation in a large proportion of patients. In fact, peptic ulcers with bleeding is a common and feared complication. Doctors are constantly seeking ways to avoid the side effects of radiation therapy and drug regiments, and for such trials there is an obvious need for an objective method to monitor the response. Calprotectin now stands out as a very promising tool for this purpose.

Pharmaceutical companies are constantly seeking new and better drugs to avoid the problems Just mentioned. When promising chemical compounds are found, extensive testing of effects and side effects must be performed in animals before human trials may be considered. Even in this respect, calprotectin assays in the animals will be wellcome. We have already found that the NSAID's give similar increases in fetal calprotectin levels in humans and rats, which suggests that this system will work for one of the most important type of drugs. Since activation of neutrophil granulocytes and release of calprotectin is the result of irritation or inflammation irrespective of the causative agent, there is a reason to belive that calprotectin assays will have a general application in drug testing.

C: Determination of calprotectin levels in monitoring bone marrow depression.

Among the most serious and often fatal complications to the use of drugs are the toxic effects on the bone marrow. This may cause fatal bleeding or infection due to lack of platelets or neutrophil granulocytes, or anemia due to lack of red cells.

In a series of patients with leukemia treated with cytotoxic drugs prior to bone marrow transplantation, the plasma calprotectin levels dropped to barely detectable levels during the period of severe bone marrow depression. When there was a take of the transplant, the calprotectin rapidly returned to normal levels. Calprotectin levels in stools will probably follow a similar pattern since more than 70 per cent of neutrophil granulocytes migrate into the intestinal lumen. Low fecal calprotectin levels may therefore be an early and sensitive sign of toxic effects on the bone marrow both in man and experimental animals.

References

1. Best WR, Becktel JM, Singleton JW, Kern F Jr. Development of a Crohn's disease activity index. Gastroenterology 1976;70:439–444.
2. Van Hees P A M, Van Elteren PH, Van Lier HJJ, Van Tongeren JHM. An index of inflammatory activity in patients with Crohn's disease. Gut 1980;21:279–286.
3. Harvey RF, Bradshaw JM. A simple index of Crohn's disease activity. Lancet 1980;i:514.
4. Meyers S, Wolke A, Field SP, Feuer EJ, Johnson JW, Janowitz HD. Fecal $\alpha_1$-antitrypsin measurements: An indicator of Crohn's disease activity. Gastroenterology 1985;89:13–18.
5. Karbach U, Ewe K, Bodenstein H. $\alpha_1$-antitrypsin, a reliable endogenous marker for intestinal protein loss and it's application in patients with Crohn's disease. Gut 1983;24:718–723.
6. Grill BB, Hillemeier AC, Gryboski JD. Fecal $\alpha_1$-antitrypsin clearance in patients with inflammatory bowel disease. J.Pediatr Gastroenterol Nutr 1984;3:56–61.
7. Thomas DW, Sinatra FR, Merrit RJ. Random fecal $\alpha_1$-antitrypsin concentration in children with gastrointestinal disease. Gastroenterology 1981;80:776–782.
8. Segal AW, Munro JM, Ensell J, Sarner M. $^{111}$Indium tagged leukocytes in the diagnosis of inflammatory bowel disease. Lancet 1981;ii:230–231.
9. Saverymuttu SH, Peters AM, Hodgson HJ, Chadwick VS, Lavender JP. $^{111}$Indium leukocyte scanning in small-bowel Crohn's disease. Gastrointest Radiol 1983;8:157–161.
10. Saverymuttu SH. Clinical remission in Crohn's disease-assessment using fecal $^{111}$In granulocyte excretion. Digestion 1986;33:74–79.
11. Park RHR, McKillop JH, Duncan A, MacKenzie JF, Russel RI. Can $^{111}$indium autologous mixed leukocyte scanning accurately assess disease extent and activity in Crohn's disease?0 Gut 1988;29:821–825.
12. Pullmann WE, Sullivan PJ, Barrat PJ, Lising J, Booth JA, Doe WF, Assessment of inflammatory bowel disease activity by $^{99}$Technetium phagocyte scanning. Gastroenterology 1988;95:989–996.
13. Nelson RL, Subramanian K, Gasparaitis A, Abcarian H, Pavel DG. $^{111}$Indium labelled granulocyte scan in the diagnosis and management of acute inflammatory bowel disease. Dis Colon Rectum 1990;33:451–457.
14. Bohbouth GE. General discussion. In: Bohbouth GE. Activity related abnormalities in inflammatory bowel disease. University Hospital Leiden, Holland, 1988:105–114.
15. Becker W, Fischback W, Weppler M, Mosl B, Jacoby G, Börner W. Radiolabelled granulocytes in inflammatory bowel disease; diagnostic possibilities and clinical indications. Nucl Med Commun 1988;9:693–701.
16. Becker W. Schomann E, Fischbach W, Börner W, Gruner KR. Comparison of $^{99m}$Tc-HMPOA and $^{111}$In-oxine 16. labelled granulocytes in man: first clinical results. Nucl Med Commun 1988;9:435–447.
17. Buxton-Thomas MS, Dickinson RJ, Maltby P, Hunter JO, Wraight EP. Evaluation of indium scintigraphy in patients with active inflammatory bowel disease. Gut 1984;2:1372–1375.
18. Crama-Bohbouth GE, Arndt JW, Pena AS, Verspaget HW, Tjon A Tham RTO, Weterman IT, Pauwels EKJ, Lamers CBHW. Value of [111]Indium granulocyte scintigraphy in the assessment of Crohn's disease of the small intestine: Prospective investigation. Digestion 1988;40:227–236.
19. Schölmerich J, Schmidt E, Schümichen C, Billmann P, Schmidt H, Gerok W. Scintigraphy assessment of bowel involvement and disease activity in Crohn's disease using $^{99m}$Tc-hexamethyl propylene amine oxide as leukocyre label. Gastroenterology 1988;95:1287–1293.
20. Arndt JW, Crama-Bohbouth GE, Verspaget HW, Blok D, Tham RTOTA, Weterman IT, Lamers CBtFW, Pauwells EKJ. Image quality and radiopharmaceutical parameters of [111]Indium granulocytes in scintigraphy of inflammatory bowel disease. Eur J Nucl Ned 1989;15:197–200.
21. Kordossis T, Joseph AEA, Cane JN, Bridges CE, Griffin GE. Fetal leukocytosis, [111]Indium labelled autologous polymorphonuclear leukocyte abdominal scanning, and quantitative fetal [111]Indium excretion in acute gastroenteritis and enterophatogen carriage. Dig Dis Sci 1988;33:1383–1390.
22. Dale I, Brandtzaeg P, Fagerhol MK, Scott H. Distribution of a new myelomonocytic antigert (L-1) in human peripheral blood leukocytes. Am J Clin Phatol 1985;84:24–34.
23. Fagerhol MK, Andersson KB, Naess-Andresen CF, Brandtzaeg P, Dale I. Calprotein (The L1 leukocyte protein). In: Vana L, Smith J R, Dedman, eds. Stimulus response coupling: The role of intracellular calcium-binding proteins. Boca Raton: CRC Press Inc., 1990:187–210.
24. Dale I, Fagerhol MK, Naesgaard I, Purification and partial characterization of a highly immunogenic human leukocyte protein, the L-1 antigen. Eur J Biochem 1983;134:1–6.
25. Steinbakk M, Naess-Andersen CF, Lingaas E, Dale I, Brandtzaeg P, Fagerhol MK. Antimicrobial action of calcium binding leukocyte L-1 protein, calprotectin. Lancet 1990;336:763–765.
26. Berntzen HB, Munthe E, Fagerhol MK. The major granulocyte protein L1 as an indicator of inflammatory joint disease. Scand J Rheumatol 1988;76 (Suppl):251–256.
27. Røseth AG, Schjønsby H, Aadland E, Fagerhol MK, Vatn M. Fecal calprotectin: A new marker of disease activity in IBD. Scan J Gastroenterol 1990;25 (Suppl):91.
28. Crama-Bohbouth G, Pena AS, Blemond I, Verspaget HW, Blok D, Arndt JW, Wetermann IT, Pauwels EKJ, Lamers CBHW. Are activity indices helpful in assessing active Intestinal inflammation in Crohn's disease? Gut 1989;30:1236–1240.
29. Brignola C, Campieri M, Bazzocchi G, Farruggia P, Tragnone A, Lanfranchi GA. A laboratory index for predicting relaps in asymptotic patients with Crohn's disease. Gastroenterology 1986;91:1490:1494.
30. Cook WT, Prior P. Determining disease activity in inflammatory bowel disease. J. Clin Gastroenterol 1984;6:17–25–
31. Fliedner SH, Cronkite EP, Robertson JS. Granulopoesis, senescence and random loss of neutrophilic granulocytes in human beings. Blood 1964;24:404–414.
32. Crossley JR, Elliot RB. Simple method for diagnosing protein-losing enterophaties. BMJ 1977:428–29.
33. Winawer SJ, Miller D. Screening for colorectal cancer. Bulletin of the World Healt Organization, 1987; 65 (1);105–11.
34. Fenoglio CM, Pascal RR. Colorectal adenoma and cancer. 1982; 50; 2061–08.
35. Simon JB. Occult blood screening for colorectal carcinoma: A critical review. Gastroenterology, 1985; 88; 820–37.
36. Letsou , Ballantyne GH, Zdon MJ, Zucker KA, Modlin IM. A comparison of the fecal occult blood test and endoscopic examination. Dis Colon Rectum, 1987; 30; 839–43.
37. Windeler J, Köberling J. Colorectal carcinoma and Haemoccult. Int J Colorectal Dis, 1987; 2; 223–28.
38. Røseth AG, Fagerhol MK, Aadland E, Schjønsby H. Assessment of the neutrophil dominationg protein calprotectin in fetes; a methodological study. Scand J Gastroenterol 1992; In press.
39. Dale I, Brandtzaeg P. Expression of the epithelial L1 as an immunohistochemical marker of squamous cell carcinoma of the lung. Histopathology 1989; 14; 493– 502.
40. Dale I: The Human Leuocyte L1 protein (Calprotectin): Purification, characterization and distribution analyses in blood and tissues. Doctoral thesis, 1991, University of Oslo, Norway.
41. Belenko M, Chanana AD, Joel DD, Fagerhol, MK, Janoff A, Tracing the leukocyte marker protein in lung fluids and draining lymph nodes during endotoxemia in sheep. Amer Rev Reap Dis; 133(5), 866, 1986).

Having described our invention, we claim:

1. An immunological method for screening for the presence of inflammatory bowel disease or gastrointestinal cancer in mammals comprising the steps of:

collecting a fecal sample or sample of the gastrointestinal tract; and measuring the amount of calprotectin in said sample by immunological means wherein an elevated amount of calprotectin is associated with the presence of inflammatory bowel disease or gastrointestinal cancer.

2. The method according to claim 1, wherein said measuring further comprises detecting calprotectin by means of immunological methods which comprises contacting said sample with at least one reagent containing at least one antibody which binds with specificity to calprotectin.

3. The method according to claim 2, further comprising the steps of:

coating a microtiter plate with a first antibody which specifically binds to calprotectin to produce a coated microtiter plate;

contacting said sample with said coated microtiter plate;

adding an enzyme conjugated second antibody to said coated microtiter plate wherein said second antibody binds to calprotectin;

incubating said coated microtiter plate under conditions such that said second antibody binds to calprotectin present on said coated microtiter plate;

washing said coated microtiter plate;

adding a substrate of said enzyme to said coated microtiter plate; and quantitating the action of said enzyme on said substrate.

4. The method according to claim 2, wherein said antibody is produced from immunization of a mammal with chromatographically pure calprotectin.

5. The method according to claim 4, wherein said mammal is a rabbit.

6. The method according to claim 2, wherein said coated plate is optionally washed at least one of, prior to contacting with sample; and prior to adding said second antibody.

7. The method according to claim 2, wherein said first and second antibodies are the same.

* * * * *